United States Patent
Marash et al.

(10) Patent No.: US 9,233,092 B2
(45) Date of Patent: *Jan. 12, 2016

(54) COMPOSITIONS AND METHODS FOR INHIBITING GASTRIC ACID SECRETION USING DERIVATIVES OF SMALL DICARBOXYLIC ACIDS IN COMBINATION WITH PPI

(75) Inventors: Michael Marash, Rishon Lezion (IL); Aleksey Kostadinov, Rehovot (IL); Tal Atarot, Tel Mond (IL)

(73) Assignee: Vecta, Ltd., Rehovot (IL)

( * ) Notice: Subject to any disclaimer, the term of this patent is extended or adjusted under 35 U.S.C. 154(b) by 687 days.

This patent is subject to a terminal disclaimer.

(21) Appl. No.: 12/309,563

(22) PCT Filed: Jul. 19, 2007

(86) PCT No.: PCT/IB2007/002028
§ 371 (c)(1),
(2), (4) Date: Jul. 13, 2009

(87) PCT Pub. No.: WO2008/012621
PCT Pub. Date: Jan. 31, 2008

(65) Prior Publication Data
US 2009/0274766 A1 Nov. 5, 2009

Related U.S. Application Data

(60) Provisional application No. 60/832,944, filed on Jul. 25, 2006, provisional application No. 60/857,132, filed on Nov. 7, 2006.

(51) Int. Cl.
*A61K 31/22* (2006.01)
*A61K 31/225* (2006.01)
(Continued)

(52) U.S. Cl.
CPC ............... *A61K 31/22* (2013.01); *A61K 31/225* (2013.01); *A61K 9/2081* (2013.01); *A61K 9/2086* (2013.01);
(Continued)

(58) Field of Classification Search
CPC . A61K 31/22; A61K 31/4439; A61K 9/2081; A61K 9/5084; A61K 9/2086; A61K 9/5094; A61K 31/19; A61K 31/225; A61K 31/522; A61K 33/10; A61K 36/534; A61K 45/00; A61K 2300/00
USPC ................. 424/497, 462, 469, 470, 472, 474; 514/546, 338, 574, 784
See application file for complete search history.

(56) References Cited

U.S. PATENT DOCUMENTS 2,343,011 A * 2/1944 Huppert .................. C08L 89/00
106/156.22
4,255,431 A 3/1981 Junggren et al.
(Continued)

FOREIGN PATENT DOCUMENTS

CN 1122109 A 5/1996
EP 05129 A1 10/1979
(Continued)

OTHER PUBLICATIONS

International Search Report for PCT/IB2007/002028 (WIPO, Aug. 5, 2008), 3 pages.*
(Continued)

*Primary Examiner* — Anna Pagonakis
*Assistant Examiner* — Miriam Levin
(74) *Attorney, Agent, or Firm* — Cooley LLP; Ivor R. Elrifi; Christina K. Stock (57) ABSTRACT

The present invention is related to novel oral compositions comprising an irreversible gastric $H^+/K^+$-ATPase proton pump inhibitor (PPI) as a gastric acid secretion inhibitor and one or more aliphatic carboxylic acid derivative molecules which activate parietal cells, wherein the derivatives possess delayed or sustained enhancement effect on the PPI activity compared to the non-derivatized acid molecules. The present invention further relates to a method of using such compositions to reduce gastric acid secretion in a mammal.

14 Claims, 1 Drawing Sheet

(51) Int. Cl.

| | | |
|---|---|---|
| *A61K 31/4439* | (2006.01) | |
| *A61K 9/14* | (2006.01) | |
| *A61K 31/19* | (2006.01) | |
| *A61K 31/194* | (2006.01) | |
| *A61K 31/44* | (2006.01) | |
| *A61K 31/522* | (2006.01) | |
| *A61K 9/16* | (2006.01) | |
| *A61K 9/20* | (2006.01) | |
| *A61K 9/24* | (2006.01) | |
| *A61K 9/26* | (2006.01) | |
| *A61K 9/28* | (2006.01) | |
| *A61K 9/48* | (2006.01) | |
| *A61K 45/00* | (2006.01) | |
| *A61K 45/06* | (2006.01) | |
| *A61P 1/04* | (2006.01) | |
| *A61P 31/04* | (2006.01) | |
| *A61P 43/00* | (2006.01) | |
| *A61K 33/10* | (2006.01) | |
| *A61K 36/534* | (2006.01) | |
| *A61K 9/50* | (2006.01) | |

(52) U.S. Cl.
CPC .............. *A61K 9/5084* (2013.01); *A61K 31/19* (2013.01); *A61K 31/522* (2013.01); *A61K 33/10* (2013.01); *A61K 36/534* (2013.01); *A61K 45/00* (2013.01); *A61K 2300/00* (2013.01)

(56) References Cited

U.S. PATENT DOCUMENTS

| | | | |
|---|---|---|---|
| 4,716,153 A | 12/1987 | Morishita et al. | |
| 4,758,579 A | 7/1988 | Kohl et al. | |
| 4,767,627 A | 8/1988 | Caldwell et al. | |
| 4,786,505 A | 11/1988 | Lovgren et al. | |
| 4,853,230 A | 8/1989 | Lovgren et al. | |
| 5,093,738 A | 3/1992 | Watanabe et al. | |
| 5,137,729 A | 8/1992 | Kuroya et al. | |
| 5,238,686 A | 8/1993 | Eichel et al. | |
| 5,559,152 A | 9/1996 | Komissarova et al. | |
| 5,626,875 A * | 5/1997 | Ballester Rodes ... | A61K 9/5078 424/451 |
| 5,731,002 A | 3/1998 | Olovson et al. | |
| 5,750,531 A | 5/1998 | Lee et al. | |
| 5,800,832 A | 9/1998 | Tapolsky et al. | |
| 5,840,737 A | 11/1998 | Phillips | |
| 5,972,389 A | 10/1999 | Shell et al. | |
| 6,093,738 A | 7/2000 | Karimian et al. | |
| 6,132,768 A | 10/2000 | Sachs et al. | |
| 6,136,344 A | 10/2000 | Depui et al. | |
| 6,159,498 A | 12/2000 | Tapolsky et al. | |
| 6,228,400 B1 | 5/2001 | Lee et al. ..................... | 424/489 |
| 6,284,271 B1 * | 9/2001 | Lundberg et al. ............. | 424/466 |
| 6,296,876 B1 | 10/2001 | Odidi et al. | |
| 6,328,993 B1 | 12/2001 | Linder et al. | |
| 6,350,468 B1 | 2/2002 | Sanso | |
| 6,489,346 B1 | 12/2002 | Phillips | |
| 6,645,988 B2 | 11/2003 | Phillips | |
| 6,699,885 B2 * | 3/2004 | Phillips ................ | A61K 9/0007 424/717 |
| 6,780,882 B2 | 8/2004 | Phillips | |
| 6,815,414 B2 | 11/2004 | Chowers et al. | |
| 7,211,568 B2 | 5/2007 | Liu et al. | |
| 7,271,146 B2 | 9/2007 | Glozman | |
| 7,803,817 B2 | 9/2010 | Kostadinov et al. | |
| 7,918,908 B2 | 4/2011 | Nahey et al. | |
| 7,981,908 B2 | 7/2011 | Kostadinov et al. | |
| 2001/0020005 A1 | 9/2001 | Chowers et al. | |
| 2003/0049204 A1 | 3/2003 | Leyland-Jones ............... | 424/9.1 |
| 2003/0175360 A1 * | 9/2003 | Luzzatti ......................... | 424/653 |
| 2003/0235628 A1 | 12/2003 | Taneja et al. | |
| 2004/0067875 A1 | 4/2004 | Lai et al. ........................ | 514/6 |
| 2004/0106634 A1 | 6/2004 | Satoh et al. ................... | 514/275 |
| 2004/0248942 A1 | 12/2004 | Hepburn et al. | |
| 2005/0112213 A1 * | 5/2005 | McCullough ...... | A61K 31/7024 424/686 |
| 2005/0181052 A1 | 8/2005 | Patel et al. | |
| 2005/0232992 A1 | 10/2005 | Devane et al. | |
| 2005/0239845 A1 | 10/2005 | Proehl et al. | |
| 2005/0244538 A1 * | 11/2005 | Andersen et al. .................. | 426/3 |
| 2006/0127489 A1 * | 6/2006 | Crothers et al. .............. | 424/490 |
| 2006/0135406 A1 | 6/2006 | Glozman et al. | |
| 2006/0183779 A1 * | 8/2006 | Brauns ................. | C07D 401/12 514/338 |
| 2006/0210604 A1 * | 9/2006 | Dadey et al. ................... | 424/427 |
| 2006/0257467 A1 * | 11/2006 | Kostadinov et al. .......... | 424/451 |
| 2009/0274766 A1 | 11/2009 | Marash et al. | |
| 2009/0304790 A1 * | 12/2009 | Nilsson et al. ................ | 424/464 |
| 2010/0247634 A1 | 9/2010 | Kostadinov et al. | |
| 2011/0111039 A1 | 5/2011 | Kostadinov et al. | |
| 2011/0250268 A1 | 10/2011 | Kostadinov et al. | |

FOREIGN PATENT DOCUMENTS

| | | |
|---|---|---|
| EP | 124495 A2 | 11/1984 |
| EP | 174726 A1 | 3/1986 |
| EP | 259174 A1 | 3/1988 |
| EP | 322133 A1 | 6/1989 |
| EP | 404322 A1 | 12/1990 |
| EP | 0696921 B1 | 2/1996 |
| EP | 1087783 A2 | 4/2001 |
| EP | 1917959 A1 | 5/2008 |
| EP | 07804623 | 10/2009 |
| GB | 2163747 A | 3/1986 |
| GB | 2 394 895 | 5/2004 |
| JP | 60193917 | 10/1985 |
| JP | 2005519901 A | 7/2005 |
| RU | 2205028 C2 | 5/2003 |
| RU | 2240110 C2 | 11/2004 |
| WO | WO-9006925 A1 | 6/1990 |
| WO | WO 91/13337 A1 | 9/1991 |
| WO | WO-9119711 A1 | 12/1991 |
| WO | WO-9119712 A1 | 12/1991 |
| WO | WO-9401099 A1 | 1/1994 |
| WO | WO-9427988 A1 | 12/1994 |
| WO | WO-9501977 A1 | 1/1995 |
| WO | WO-9725030 A1 | 7/1997 |
| WO | WO-9965513 A2 | 12/1999 |
| WO | WO-0078293 A1 | 12/2000 |
| WO | WO-0122985 A1 | 4/2001 |
| WO | WO-0151050 A1 | 7/2001 |
| WO | WO 03/061584 A2 | 7/2003 |
| WO | WO-03086267 A2 | 10/2003 |
| WO | WO 2004/112756 A1 | 12/2004 |
| WO | WO-2005020879 A2 | 3/2005 |
| WO | WO 2005/065664 | 7/2005 |
| WO | WO 2006/037342 A2 | 4/2006 |
| WO | WO-2006120500 A1 | 11/2006 |
| WO | WO 2008/012621 A2 | 1/2008 |

OTHER PUBLICATIONS

International Preliminary Report on Patentability for PCT/IB2007/002028 (WIPO, Mar. 31, 2009), 4 pages.*

International Search Report from PCT/IB2009/006176 dated Dec. 8, 2009.

European Examination Report, Application No. 07804623.2 Feb. 9, 2010.

Mashkovsky et al. "Medicaments." Moscow: OOO Novaya Volna, 2001. 1:11.

Vitale et al. "Succinic and Malic Oxidase in Gastric Hydrochloric Acid Production." *Am. J. Physiol.* 187(Nov. 1956):427-431.

Ammar et al., "Syntaxin 3 is required for cAMP-induced acid secretion: streptolysin O-permeabilized gastric gland model", *Am. J. Physiol.—Gastrointestinal Liver Physiol.*, 282:G23-G33 (2002).

Ayalon et al., "Does Luminal Gastrin Stimulate Gastric Acid Secretion?", *Am. J. Surg.*, 141:94-97 (1981).

Chand et al., "Sleep dysfunction in patients with gastro-oesophageal reflux disease: prevalence and response to GERD therapy, a pilot study", *Aliment Pharmacol. Ther.2004*, 20:969-974 (2004).

(56) References Cited

OTHER PUBLICATIONS

Chen et al., "Sleep Symptoms and Gastroesophageal Reflux", *J. Clin. Gastroenterol.*, 42(1):13-17 (2008).
De Graef et al., "Influence of the Stimulation State of the Parietal Cells on the Inhibitory Effect of Omeprazole on Gastric Acid Secretion in Dogs," Gastroenterology, 91:333-337 (1985).
Fiddian-Green et al., "A physiological role for luminal gastrin?" *Surgery*, 83(6):663-668 (1978).
Hatlebakk et al., "Pharmacokinetic Optimisation in the Treatment of Gastro-Oesophageal Reflux Disease", *Clin. Pharmacokinet.*, 31(5):386-406 (1996).
Hunt et al, "The Effect of Citric Acid and Its Sodium Salts in Test Meals on the Gastric Outputs of Acid and of Chloride", *J. Physiol.*, 230(1):171-184 (1973).
International Search Report for PCT/IB07/01078 dated Apr. 9, 2009.
International Search Report for PCT/IB05/02223 dated Mar. 28, 2006.
Kuroda et al., "Inhibitory Effect of Fumaric Acid and Dicarboxylic Acids on Gastric Ulceration in Rats", *Arch. Mt. Pharmacodyn.*, 226:324-330 (1977).
Maliuk et al, "Effect of Succinate Sodium on the Acid Forming and Motor Function of the Stomach in Patients with Tuberculosis", *rachebnoe Delo*, 10:60-62 (1981) (Abstract Only).
Martindale, "Supplementary Drugs and Other Substances", Thirty-second Ed., p. 1616.
Merritt, A.M., "The Equine Stomach: A Personal Perspective (1963-2003)", 49th Annual Convention of the American Association of Equine Practitioners, www.ivis.org, Nov. 21, 2003.
Morii et al., "The Potency of Substituted Benzimidazoles such as E3810, Omeprazole, Ro 18-5364 to Inhibit Gastric $H^+,K^+$-ATPase is Correlated with the Rate of Acid-Activation of the Inhibitor", *Biochem. Pharmacol.*, 39(4):661-667 (1990).
Morrell et al., "Absorption of Pentagastrin from Gastrointestinal Tract in Man," *Lancet*, 2(7937):712 (1975) (Abstract Only).
Nagata et al., "Inhibitory Action of Lansoprazole and Its Analogs Against *Helicobacter pylori*: Inhibition of Growth is Not Related to Inhibition of Urease," *Antimicrobial Agents and Chemotherapy*, 39(2):567-570 (1995).
Nobuhara et al., "Vinegar is a Dietary Mild Irritant to the Rat Gastric Mucosa", *Japanese J. Pharmacol.*, 41:101-108 (1986).
Pokrovsky et al., "On the Role of Succinate in Energy Supply of the Hydrochloric Acid Secretion in the Gastric Mucosa", *J. Physiol.*, 10:1567-1573 (1973) (English Abstract Only).
Sachs, G., "Improving on PPI-based therapy of GORD", *Eur. J. Gastroenterol. Hepatol.*, 13(Suppl. 1):S35-S41(2001).
Scarpignato et al., "Acid Suppression Therapy: Where Do We Go from Here?" *Dig. Dis.*, 24:11-46 (2006).
Shaker et al., "Nighttime Heartburn Is an Under-Appreciated Clinical Problem That Impacts Sleep and Daytime Function: The Results of a Gallup Survey Conducted on Behalf of the American Gastroenterological Association", *Am. J. Gastroenterol.*, 98(7):1487-1493 (2003).

Teyssen et al., "Maleic and Succinic Acid as Stimulants of Acid Production in Isolated Native Rat Gastric Parietal Cells", *Esophageal, Gastric and Duodenal Disorders*, G1456:A333 (1999 (Abstract Only).
Teyssen et al., "Maleic acid and succinic acid in fermented alcoholic beverages are the stimulants of gastric acid secretion", *J. Clin. Invest.*, 103(5):707-713 (1999).
Tytgat, G.N., "Shortcomings of the first-generation proton pump inhibitors", *Eur. J. Gastroenterol. Hepatol.*, 13(Suppl. 1):S29-S33 (2001).
Written Opinion of the International Search Authority for PCT/IB07/01078 dated Apr. 9, 2009.
Written Opinion of the International Search Authority for PCTIB05/02223 dated Mar. 28, 2006.
Yau et al., "A comparison of omeprazole and ranitidine for prophylaxis against aspiration pneumonitis in emergency Caesarean section", *Anaesthesia*, 47:101-104 (1992).
Postius et al. "The Novel Proton Pump Inhibitor Pantoprazole Elevates Intragastric pH for a Prolonged Period When Administered Under Conditions of Stimulated Gastric Acid Secretion in the Gastric Fistula Dog." *Life Sciences*. 49.14(1991):1047-1052.
Sokolov et al. "Combined Medicaments." *Zoo Industry*. No. 4 (2004). <http://www.vettorg.net/magazines/3/2004/90/553/> (No English translation available).
"Omeprazole: Administration." Gold Standard, 2010.
"Secretory Functions of the Alimentary Tract." *Textbook of Medical Physiology*. Guyton et al., eds. Philadelphia: W. B. Saunders Co. 10th ed. Ch. 64. (2000):738-753.
*Burger's Medicial Chemistry and Drug Discovery*. Abraham et al., eds. 6th ed. Hoboken, NJ: John Wiley & Sons, Inc. 4(2003):102-115.
MacDonald et al. "Glyceraldehyde Phosphate and Methyl Esters of Succinic Acid." *Diabetes*. 37(1988):997-999.
"Lansoprazole." Gold Standard Inc. (2010).
"Omeprazole." Gold Standard Inc. (2010).
Ranucci et al. "Polymeric Pharmaceutical Excipients." *Pharmaceutical Dosage Forms: Disperse Systems*. New York: Marcel Dekker, Inc. Lieberman et al., eds. 2nd ed. 3(1998):243, 272, 282.
Sherwood. "The Digestive System." *Human Physiology: From Cells to Systems*. Belmont, CA: Brooks/Cole. 5th ed. (2004):591-616.
Wan et al. "Matrix Swelling: A Simple Model Describing Extent of Swelling of HPMC Matrices." *Int. J. Pharmaceutics*. 116(1995):159-168.
Talpes et al., "Esomeprazole MUPS 40 mg tablets and esomeprazole MUPS 40 mg tablets encapsulated in hard gelatine are bioequivalent", International Journal of Clinical Pharmacology and Therapeutics, Jan. 2005, vol. 43 (51-56).
The Merck Index Online, "Colloidal Bismuth Subcitrate", CAS Registry No. 57644-54-9, Royal Society of Chemistry, 1 page (2013).
FDA Guidelines for Industry Non-Sterile Semisolid Dosage Forms, 40 pages (May 1997).
International Preliminary Report on Patentability for international application PCT/IB2009/006176 dated Nov. 17, 2010, 6 pages.

* cited by examiner

COMPOSITIONS AND METHODS FOR INHIBITING GASTRIC ACID SECRETION USING DERIVATIVES OF SMALL DICARBOXYLIC ACIDS IN COMBINATION WITH PPI

RELATED APPLICATIONS

This application is a national stage application, filed under 35 U.S.C. §371, of International Application No. PCT/IB2007/002028, filed on Jul. 19, 2007, and which claims the benefit of U.S. Provisional Application Nos. 60/832,944, filed Jul. 25, 2006, and 60/857,132, filed Nov. 7, 2006, each disclosure of which is herein incorporated by reference.

FIELD OF THE INVENTION

The present invention relates to novel oral compositions for inhibition of gastric acid secretion comprising a proton pump inhibitor in conjunction with one or more derivatives of aliphatic monocarboxylic, dicarboxylic or tricarboxylic acids, wherein the derivatives possess delayed and/or sustained enhancement effect on the PPI activity or accelerated drug stability compared to the non-derivatized acid molecules. The present invention further relates to a method of using such compositions to reduce gastric acid secretion in a mammal.

BACKGROUND OF THE INVENTION

A wide number of pathological conditions are characterized by the need to suppress gastric acid secretion. Such conditions include, but are not limited to Zollinger/Ellison syndrome (ZES), gastroesophageal reflux disease (GERD), peptic ulcer disease, duodenal ulcers, esophagitis, and the like. Conditions such as peptic ulcers can have serious complications and represent some of the most prevalent diseases in industrialized nations.

Presently, the main therapies employed in the treatment of GERD and peptic ulcer diseases include agents for reducing the stomach acidity, for example by using the histamine $H_2$-receptor antagonists or proton pump inhibitors (PPIs). PPIs act by inhibiting the parietal cell $H^+/K^+$ ATPase proton pumps responsible for acid secretion from these cells. PPIs, such as omeprazole, and its pharmaceutically acceptable salts are disclosed for example in EP 05129, EP 124495 and U.S. Pat. No. 4,255,431.

PPI agents are acid-labile pro-drugs that are usually administered in enteric-coated granules and are weak bases. Following absorption in the small intestine, PPIs preferentially accumulate within the acid milieu of the acid-secreting parietal cells. The acid environment within the acid milieu of parietal cells causes the conversion of the pro-drugs into the active sulfenamides, which are the active agents that bind and inhibit the parietal cell $H^+/K^+$ ATPase pumps. Thus, pre-activation of parietal cells is required for the conversion of PPIs to its active protonated form. The pre-activation of parietal cells is usually achieved by meal ingestion that initiates gastrin-dependent parietal cell activation. Indeed, patients are instructed to take PPI one hour prior to meal intake in order to ensure that parietal cells are activated when the PPI reaches the parietal cells via blood stream.

Despite their well-documented efficacy, PPIs have notable limitations. The conversion of PPI to its active form requires pre-activation of parietal cells. The pre-activation of parietal cells is normally achieved by ingestion of food. Thus, the PPI must be taken prior to ingestion of food in order to synchronize between the pre-activation of parietal cells and PPI absorption in blood. Furthermore, PPIs have a relatively low onset of pharmacological action which may require several days to achieve steady state of maximum acid suppression and symptom relief, limiting their usefulness in on-demand GERD therapy (Sachs G, Eur J Gastroenterol Hepatol. 2001; 13 Suppl 1:S35-41).

Moreover, PPIs fail to provide 24-h suppression of gastric acid and nocturnal acid breakthrough leads to night time heartburn and pain in GERD patients even on twice-daily dosing of PPIs (Tytgat G N, Eur J Gastroenterol Hepatol. 2001; 13 Suppl 1:S29-33; Shaker R. et al., Am. J. of Gastroenterology, 98 (7), 2003). Finally, these drugs exhibit substantial intra- and inter-patient variability in pharmacokinetics (Hatlebakk et al., Clin Pharmacokinet. 1996; 31(5):386-406). Thus, an improvement of PPI unmet medical needs is a well-recognized challenge in gastroenterology.

Maleic acid and succinic acid, chemically characterized as four-carbon dicarboxylic acids, are powerful stimulants of gastric acid output (Teyssen et al., J. Clin Invest. 1999 103(5): 707-713). Teyssen et al. studied the stimulation of gastric acid secretion in fermented alcoholic beverages (containing such compounds) (e.g., beer and wine). Interestingly, maleic acid and succinic acid were found to stimulate gastric acid output in humans as that produced by beer, champagne, wine, and pentagastrin (a powerful exogenous stimulus to induce acid secretion), but without gastrin being their mediator of action (Teyssen et al., J. Clin Invest. 1999)

U.S. Pat. No. 5,559,152 discloses that a mixture of succinic acid and citric acid in the dose of 3.5 mg/kg is capable of inducing gastric acid output in dogs as reflected by significant reduction in the pH of the gastric juice measured on an empty stomach 40 min following drug administration. This patent further discloses that succinic and citric acid stimulate acid output in healthy human volunteers.

Pokrovskiy et al. (Physiologicheskiy Z'urnal 10:1567-1573, 1973) also disclosed that molecules involved in the mitochondrial respiration circle (Krebs cycle) such as pyruvate, succinate, alpha-ketoglutarate, malate or glucose may stimulates proton secretion in ex vivo model of frog mucosa.

Co-pending applications PCT/IB2005/002223 (published as WO 2006/120500 and US 2006/0257467) describe oral compositions comprising a PPI as a gastric acid secretion inhibitor and one or more small dicarboxylic acid molecules. The small carboxylic acid molecules were capable of enhancing the anti-acid activity of PPI in the stomach.

U.S. Pat. Nos. 6,489,346; 6,645,988; and 6,699,885; to Phillips jointly the "Phillips patents") disclose pharmaceutical compositions and methods of treating acid-caused gastrointestinal disorders using oral compositions consisting of a PPI, at least one buffering agent and specific parietal cell activators. The parietal cell activators disclosed in the Phillips patents include, for example, chocolate, sodium bicarbonate, calcium, peppermint oil, spearmint oil, coffee, tea and colas, caffeine, theophylline, theobromine and amino acids residues. As indicated in the Phillips patents, all these proposed parietal cell activators induce the release of endogenous gastrin leading to stimulatory effects on acid secretion.

The development of an effective treatment for pathologies in which inhibition of gastric acid secretion is required would fulfill a long felt need. Despite the wide-spread use of PPIs, a need still exist for increasing the PPI efficacy, e.g., prolonged effect to control night time acid breakthrough, greater effect at reduced dosage, meal-independent administration and control of night time acid production. Applicants' invention disclosed herein meets many of these unmet needs.

SUMMARY OF THE INVENTION

It is the object of the present invention to provide PPI-based compositions with enhanced activity in inhibition of gastric acid secretion.

In one embodiment, the present invention relates to compositions comprising a substituted benzimidazole $H^+/K^+$-ATPase proton pump inhibitor (PPI) as a gastric acid secretion inhibitor and one or more derivatives of saturated or non-saturated aliphatic carboxylic acids such as monocarboxylic, dicarboxylic or tricarboxylic acid molecules, wherein the derivatives possess delayed and/or sustained parietal cell activation or accelerated drug stability compared to the non-derivatized acid molecules, thereby enhancing the anti-secretory effect in combination with PPI. Preferred derivatives of acid molecules to be used as enhancers of the anti-secretory effect of the proton pump inhibitor are esters of aliphatic monocarboxylic, dicarboxylic or tricarboxylic acid involved in the mitochondrial respiration circle (Krebs cycle), more preferably methyl, ethyl, propyl or butyl esters of aliphatic dicarboxylic acids having between three to ten carbons in the aliphatic chain. Most preferred are methyl or ethyl esters of succinic acid or maleic acid. The present compositions may be used for treating a subject suffering from chronic or acute disorders in which suppression of acid secretion in the stomach is required.

The substituted benzimidazole proton pump inhibitors according to the present invention are compounds that inhibit the activity of the $H^+/K^+$-adenosine triphosphatase (ATPase) proton pump in the gastric parietal cells. In its pro-drug form, the PPI is non-ionized and therefore is capable of passing through the cellular membrane of the parietal cells. Once reaching the parietal cells, the non-ionized PPI moves into the acid-secreting portion of activated parietal cells, the secretory canaliculus. The PPI trapped in the canaliculus becomes protonated, thus converted to the active sulfenamide form that can form disulfide covalent bonds with cysteine residues in the alpha subunit of the proton pump, thereby irreversibly inhibiting the proton pump.

The present invention is based on the inventors surprising discovery that while specific aliphatic dicarboxylic acid molecules involved in the mitochondrial respiration circle (Krebs cycle) such as maleic acid and succinic acid can activate parietal cell, thereby enhancing the activity of proton pump inhibitors in inhibiting gastric acid secretion, specific derivatives of such acid molecules are more effective in inhibiting gastric acid secretion in combination with PPI. Without being bound by theory, it is believed that the derivatives possess delayed and/or sustained parietal cell activation or accelerated drug stability compared to the non-derivatized acid molecules, thereby enabling adequate overlap of pharmacodynamic profiles of these two components. Therefore, the synchronized activation of the parietal cells by the derivatives of the present invention maximizes the inhibition of the pumps by the PPI.

The compositions of the present invention exhibit the following advantages over the known PPI-based compositions aimed to reduce gastric acid secretion. The present compositions permit efficient pre-activation of the parietal cells by the derivatives of the present invention instead of food ingestion. Pre-activation of parietal cells by these derivatives is required in order to enable adequate overlap of pharmacodynamic profiles of the derivatives and the PPI. The combined active agents of the present compositions provide an effective solution for bed-time PPI administration in GERD patients that are instructed not to ingest food at bed-time.

The compositions according to the present invention may comprise any derivative of aliphatic monocarboxylic, dicarboxylic or tricarboxylic acid molecules, such as salts, esters, aldehydes, ketones, nitriles, alcohols, polymorphs, hydrates, or conformers, provided that the derivatives possess sustained and/or delayed parietal cell activation or accelerated drug stability compared to the non-derivatized carboxylic acid molecules. Preferred derivatives of carboxylic acid molecules are esters of such aliphatic monocarboxylic, dicarboxylic or tricarboxylic acid molecules, more preferably methyl, ethyl, propyl or butyl esters of aliphatic dicarboxylic acids having between three to ten carbons in the aliphatic chain. Most preferred derivatives are dimethyl or diethyl esters of dicarboxylic acid molecules such as dimethyl or diethyl succinic acid.

Preferred carboxylic acid molecules which are the basis of this invention are aliphatic saturated or non-saturated monocarboxylic, dicarboxylic or tricarboxylic acids involved in Krebs cycle. Most preferred aliphatic carboxylic acids are saturated or non-saturated dicarboxylic or tricarboxylic acids having between three to six carbons in the aliphatic chain such as maleic acid, succinic acid or citric acid. Also included within the scope of the present invention are other aliphatic carboxylic acid molecules involved in Krebs cycle such as for example pyruvate, α-ketoglutarate, succinyl-CoA, fumarate, or oxaloacetate.

The preferred acid molecules according to the present invention are methyl, ethyl, propyl or butyl-esters of maleic acid, succinic acid or citric acid, most preferably dimethyl-ester or diethyl-ester of succinic acid or combination thereof (for example, succinic acid di-ester in which one carboxylic end is esterified to a methyl ester and the second carboxylic end is esterified to an ethyl ester). It is also possible that the derivatives of acid molecules of the present invention are combined in a composition with the non-derivatized acid molecules and PPI in order to get both immediate and delayed or sustained effect of the acid molecules on parietal cell activation. For example in a preferred embodiment, the composition comprises a combination of succinic acid, monomethyl, dimethyl, monoethyl or diethyl succinic acid and PPI.

The compositions according to the present invention are preferably oral compositions, however, parenteral compositions are also included in the scope of the present invention. The active ingredients of the present invention are preferably formulated in a single oral dosage form, preferably a solid dosage form. In this case, the activity of the PPI and the aliphatic carboxylic acid derivative is synchronized due to the delayed and/or sustained effect of the aliphatic carboxylic acid derivative. Thus, in one embodiment the PPI and the aliphatic carboxylic acid derivative according to the present invention may be formulated as multi-layered tablets, suspension tablets, effervescent tablets, powder, pellets, granules, hard gelatin capsules comprising multiple beads, or soft gelatin capsules containing a lipid-based vehicle. Liquid dosage forms such as suspensions may be used as well. The PPI and the aliphatic carboxylic acid derivative may be physically separated in order to avoid damage to the PPI during storage.

According to one embodiment, the solid dosage form of the present invention is a capsule or a multi-layered tablet containing PPI particles coated with either enteric pH-dependent release polymers or non-enteric time-dependent release polymers and particles of the aliphatic carboxylic acid derivative. If necessary, the aliphatic carboxylic acid derivative particles are formulated as gastro retentive formulation such as bioadhesive formulation, Accordion-type formulation or floating formulation or delayed release formulation in order to extend the releasing time in the stomach. It is also possible that different aliphatic carboxylic acid derivatives will be formulated in a single oral dosage form wherein each derivative having different gastro retentive or delayed release profile.

The active ingredients of the present invention may also be formulated in separate dosage forms. For example, the aliphatic carboxylic acid derivative according to the present invention may be formulated in an oral suspension or a solid dosage form such as capsules, tablets, suspension tablets, or effervescent tablets and the PPI may be formulated in a separate solid dosage form, preferably capsules or tablets comprising beads with enteric pH-dependent release polymers or non-enteric time-dependent release polymers. The separate dosage forms may be provided as a kit containing particles of the aliphatic carboxylic acid derivative in one dosage form and the particles of PPI in a separate dosage form. In this case, the aliphatic carboxylic acid derivative particles are administered in conjunction with the PPI so that there is at least some chronological overlap in their physiological activity. The PPI and the aliphatic carboxylic acid derivative can be administered simultaneously and/or sequentially.

The active ingredients of the present invention may also be formulated in a dosage form suitable for parenteral administration such as intravenous administration, buccal delivery and subcutaneous injection. It is also possible that one of the active ingredients is administered orally (such as aliphatic carboxylic derivative molecules in tablets or capsules) and the second active ingredient (the PPI) is administered parenterally by intravenous, by buccal delivery or subcutaneous injection.

In another embodiment, the present invention is directed to a method of treating a subject suffering from a disorder in which suppression of gastric acid secretion is required or a disorder normally treated by suppression of gastric acid secretion. The method comprising administering to the subject a pharmaceutical composition comprising a PPI as a gastric acid secretion inhibitor and one or more aliphatic carboxylic acid derivatives as a PPI enhancer, wherein the derivatives possess delayed and/or sustained enhancement effect on the PPI activity or accelerated drug stability compared to the non-derivatized acid molecules.

The compositions of the present invention may be used for preventing or treating pathologies in a mammal in which inhibition of gastric acid secretion is required. Preferably the mammal is human. The compositions of the present invention are effective both in treating the pathologies and in minimizing the risk of development of such pathologies before onset of symptoms.

The pharmaceutical compositions of the present invention may be used in a wide number of pathological conditions that are treated by suppression of gastric acid secretion. Such conditions include, but are not limited to Zollinger/Ellison syndrome (ZES), gastroesophageal reflux disease (GERD), esophagitis, peptic ulcer diseases, duodenal ulcers, gastritis and gastric erosions, dyspepsia, NSAID-induced gastropathy, and the like.

The present invention also includes a pharmaceutical kit, preferably an oral pharmaceutical kit. The kit typically comprises as active ingredients a pharmaceutically effective amount of: (i) one or more aliphatic carboxylic acid derivative according to the present invention; and (ii) a substituted benzimidazole $H^+/K^+$-ATPase proton pump inhibitor. In one embodiment, the active ingredients are formulated in separate dosage unit forms. The kit may be used to treat or prevent a disorder in a subject in which suppression of gastric acid secretion is required by administering to a subject the active ingredients. The one or more aliphatic carboxylic acid derivatives are typically administered simultaneously, prior to or following the administration of the PPI.

These and further embodiments will be apparent from the detailed description and examples that follow.

DETAILED DESCRIPTION OF THE INVENTION

The compositions of the present invention provide a unique combination of PPI as a gastric acid secretion inhibitor and one or more derivatives of aliphatic monocarboxylic, dicarboxylic or tricarboxylic acid molecules as parietal cell activators, wherein the derivatives possess delayed or sustained parietal cell activation or accelerated drug stability compared to the non-derivatized acid molecules.

A "derivative" of a compound means a chemically modified compound wherein the chemical modification takes place at one or more functional groups of the compound. The derivative however, is expected to retain the pharmacological activity of the compound from which it is derived.

The compositions of the present invention may be used for preventing or treating pathologies in a mammal in which inhibition of gastric acid secretion is required. The compositions of the present invention are effective both in treating the pathologies and in minimizing the risk of development of such pathologies before onset. Such pathologies include for example: Reflux esophagitis, gastritis, duodenitis, gastric ulcer and duodenal ulcer. Furthermore, the compositions of the present invention may be used for treatment or prevention of other gastrointestinal disorders where gastric acid inhibitory effect is desirable, e.g. in patients on nonsteroidal anti-inflammatory drugs (NSAID) therapy (including low dose aspirin), in patients with Non Ulcer Dyspepsia, in patients with symptomatic gastro-esophageal reflux disease (GERD), and in patients with gastrinomas. They may also be used in patients in intensive care situations, in patients with acute upper gastrointestinal bleeding such as bleeding peptic ulcers, in patients with nonvariceal upper gastrointestinal bleeding, for prevention of stress-related mucosal bleeding, in conditions of pre- and postoperatively to prevent aspiration of gastric acid and to prevent and treat stress ulceration. Further, they may be useful in the treatment of *Helicobacter pylori* infections and diseases related to these. Other conditions well suited for treatment include, but are not limited to Zollinger-Ellison syndrome (ZES), Werner's syndrome, and systemic mastocytosis.

In one embodiment, the derivatives of the present invention possess a delayed parietal cell activation compared to the non-derivatized acid molecules. For example, the derivatives possess a parietal cell activation which starts about 15 min, 30 min, 45 min, 60 min, 75 min, 90 min, 105 min or 120 min following their administration.

In another embodiment, the derivatives of the present invention possess a sustained parietal cell activation compared to the non-derivatized acid molecules. For example, the derivatives possess parietal cell activation which prolongs for at least about 30 min, 45 min, 60 min, 75 min, 90 min, 105 min or 120 min following their administration.

In yet another embodiment, the derivatives of the present invention possess a parietal cell activation which starts about 15 min, 30 min, 45 min, 60 min, 75 min, 90 min, 105 min or 120 min following their administration and prolongs for at least about 30 min, 45 min, 60 min, 75 min, 90 min, 105 min or 120 min following their administration.

In another embodiment, the derivatives of the present invention possess accelerated drug stability (especially accelerated drug stability during storage) compared to the non-derivatized acid molecules. For example, the derivatives possess an increase in drug stability of about 25%, 50%, 75% or 100% compared to the stability of the non-derivatized acid molecules.

In a preferred embodiment, the activation of parietal cells by the derivatives of the present invention initiates at least about 30 min following derivatives administration and/or prolongs for at least about 60 min following derivatives administration.

The enhancers of the anti-secretory effect of the proton pump inhibitor according to the present invention are specific derivatives of aliphatic monocarboxylic, dicarboxylic or tricarboxylic acids, or salt thereof. Preferred acid molecules are aliphatic carboxylic acids involved in Krebs cycle. Specific preferred acid molecules are derivatives of aliphatic saturated or non-saturated dicarboxylic acids that may be used as PPI enhancers according to the present invention. Preferred aliphatic dicarboxylic acids are represented by the general formula: $HO_2C—(CH_2)_n—CO_2H$ (where n=0 to 5). Specific saturated aliphatic dicarboxylic acids are Oxalic (n=0), Malonic (n=1), Succinic (n=2), Glutaric (n=3), Adipic (n=4) and Pimelic (n=5) Acids. Preferred aliphatic dicarboxylic acid derivatives to be used as PPI enhancers according to the present invention are aliphatic dicarboxylic acids having from 2 to 6 carbon atoms, more preferably 4 carbon atoms such as succinic acid. Preferred non-saturated aliphatic dicarboxylic acid derivatives to be used according to the present invention are the four carbon maleic acid and fumaric acid.

The dicarboxylic acid derivatives that may be used are for example dicarboxylic acid esters, aldehydes (such as succinic dialdehyde), ketones (such as dimethyl 1,4-cyclohexanedione-2,5-dicarboxylate), nitriles (such as nitrile succinate), alcohols (such as diethylene glycole succinate), salts, crystalline polymorphs such as alpha or beta polymorphs, conformers, prodrugs, amides, halides, hydrates, or dicarboxylic anhydrides. Also included within the scope of the present invention are aliphatic carboxylic acid derivative molecules involved in the mitochondrial respiration circle (Krebs cycle) such as for example pyruvate, citrate, fumarate, α-ketoglutarate, succinyl-CoA or oxaloacetate.

Particular preferred examples of dicarboxylic acid derivatives that may be used in the present invention are dicarboxylic monoesters or diesters (methyl, ethyl, propyl or butyl esters such as monomethyl, dimethyl, monoethyl or diethyl esters of dicarboxylic acid molecules). Other examples of dicarboxylic acid derivatives are derivatives composed of multiple units of the dicarboxylic acid molecule (such as multiple units of succinic acid) wherein the free end carboxyl groups may be esterified with alkyl.

Other examples of succinic acid derivatives are tetramethylsuccinates, trimethylsuccinate, diethylsuccinate, dimethylsuccinate such as arabitol—5-hydroxy-1,2,3,4-tetramethyl-succinate, 4-tert-butyl-succinate, threitol-1,2,4-trimethylsuccinate, threitol-3-succinoyl-1,2,4-trimethylsuccinate, ethanediol-1,2-diethylsuccinate, propanediol-1,2-dimethylsuccinate, threitol-1,2,4-trimethyl-succinate. Other esters of succinic acid molecules are diisopropyl, disalicyl, dibutyl, benzyl hydrogen, diallyl, allyl hydrogen, isopropyl, O-methyl-6-D-glucosyl, 3-O-methyl-6-amino-6-deoxy-6-D-glucosyl, 6-amino-6-deoxy-6-D-galactosyl, buthyl, hexyl, dipropyl.

Other examples of succinic acid esters are alkenyl substituted succinic acid and ester of alkyl substituted succinic acid include monomethyl ester of octadecenyl succinic acid, dimethyl ester of octadecenyl succinic acid, monoethyl ester of octadecenyl succinic acid, diethyl ester of octadecenyl succinic acid, monooctyl ester of octadecenyl succinic acid, dioctyl ester of octadecenyl succinic acid, mononyl ester of octadecenyl succinic acid, dinonyl ester of octadecenyl succinic acid, monolauryl ester of octadecenyl succinic acid, dilauryl ester of octadecenyl succinic acid, monolauryl ester of dodecyl succinic acid, dilauryl ester of dodecyl succinic acid, monomethyl ester of hexadecyl succinic acid, dimethyl ester of hexadecyl succinic acid, monoethyl ester of hexadecyl succinic acid, diethyl ester of hexadecyl succinic acid, monomethyl ester of octadecyl succinic acid, dimethyl ester of octadecyl succinic acid, monoethyl ester of octadecyl succinic acid, diethyl ester of octadecyl succinic acid, monooctyl ester of octadecyl succinic acid, dioctyl ester of octadecyl succinic acid, monolauryl ester of octadecyl succinic acid, monolauryl ester of octadecyl succinic acid, dilauryl ester of octadecyl succinic acid, a reaction product of an alkenyl succinic acid of a propylene oligomer having 18 carbon atoms on an average and a propylene glycol, a reaction product of a polybutenyl succinic acid of a polybutene having an average molecular weight of 400 and a propylene glycol, octyl mercaptan ethylene oxide ester of octadecenyl succinic acid, octyl mercaptan propylene oxide ester of octadecenyl succinic acid, nonyl mercaptan ethylene oxide ester of octadecenyl succinic acid, nonyl mercaptan propylene oxide ester of octadecenyl succinic acid, lauryl mercaptan ethylene oxide ester of octadecenyl succinic acid, lauryl mercaptan propylene oxide ester of octadecenyl succinic acid, 5-hydroxy-3-thiapentyl ester of octadecenyl succinic acid, 6-hydroxy-3,4-dithiahexyl ester of octadecenyl succinic acid and the like.

Any pharmaceutically acceptable salt of small carboxylic acids such as succinic acid and their derivatives may be used in the present invention. Examples of such succinic acid salts are in particular, sodium succinate, disodium succinate, calcium succinate, magnesium succinate and potassium succinate as well as their known hydrates such as sodium succinate hexahydrate, disodium succinate (anhydrous).

Examples of carboxylic acids polymorphs that may be used in the present invention are maleic acid, fumaric acid, glutaric acid and succinic acid polymorphs (including crystalline, molecular adducts, nonstoichiometric inclusion compounds, stoiciometric solvates and amorphous forms).

The present invention also covers any prodrug molecules that release the active carboxylic acid derivative molecules in vivo through exposure to a particular physiologic environment or metabolic process. The term "prodrug" refers to a drug, drug precursor or modified drug that is not fully active or available until converted in vivo to its therapeutically active or available form. Such prodrug molecule might be for example any molecule that is being cleaved in vivo to release the active carboxylic acid molecule.

The compositions of the present invention comprise one or more derivative of aliphatic carboxylic acids or an analog thereof in an effective amount to possess delayed and/or sustained parietal cell activation or accelerated drug stability compared to the non-derivatized acid molecules without undue adverse side effects. The standard approximate amount of the aliphatic carboxylic acid derivative present in the compositions is preferably in an amount of 1-2500 mg, more preferably 10-1000 mg, and most preferably 50-600 mg.

In one preferred embodiment, the composition of the present invention comprises one or more aliphatic tricarboxylic acids, preferably citric acid in combination with the one or more dicarboxylic acid derivatives. The standard approximate amount of one or more tricarboxylic acids present in the compositions is preferably in an amount of 1-1000 mg, more preferably 10-1000 mg, and most preferably 50-200 mg.

In another preferred embodiment, the composition of the present invention further comprises one or more additional parietal cell activators in order to maximize the activation of parietal cells. These may include chocolate, caffeine, buffering agents such as sodium bicarbonate, calcium (e.g., calcium carbonate, calcium gluconate, calcium hydroxide, calcium acetate and calcium glycerophosphate), peppermint oil, spearmint oil, theophylline, theobromine, and amino acids such as phenylalanine and tryptophan. Such parietal cell activators are administered in an amount sufficient to produce the desired stimulatory effect without causing undesired side effects to the subject.

The compositions of the present invention further comprise a PPI that acts as an irreversible inhibitor of the gastric $H^+/K^+$-ATPase proton pump. The PPI used in the present invention can be any substituted benzimidazole compound having $H^+$, $K^+$-ATPase inhibiting activity. For the purposes of this invention, the term "PPI" shall mean any substituted benzimidazole possessing pharmacological activity as an inhibitor of $H^+$, $K^+$-ATPase, including, but not limited to, omeprazole, lansoprazole, pantoprazole, rabeprazole, dontoprazole, perprazole (s-omeprazole magnesium), habeprazole, ransoprazole, pariprazole, tenatoprazole and leminoprazole in neutral form or a salt form, a single enantiomer or isomer or other derivative or an alkaline salt of an enantiomer of the same.

Examples of gastric $H^+/K^+$-ATPase proton pump inhibitors that may be used in the present invention are disclosed for example in U.S. Pat. No. 6,093,738 that describes novel thiadiazole compounds that are effective as proton pumps inhibitors. European Patent Nos. 322133 and 404322 disclose quinazoline derivatives, European Patent No. 259174 describes quinoline derivatives, and WO 91/13337 and U.S. Pat. No. 5,750,531 disclose pyrimidine derivatives, as proton pump inhibitors. Suitable proton pump inhibitors are also disclosed for example in EP-A1-174726, EP-A1-166287, GB 2 163 747 and WO90/06925, WO91/19711, WO91/19712, WO94/27988 and WO95/01977.

In a non-limiting embodiment, the ratio between the small carboxylic acid derivative molecules, and the PPI are about 20:1 to about 1:5.

The compositions of the present invention are preferably suitable for oral administration. The PPI particles in the oral compositions according to the present invention may be either coated or non-coated. The preparation of enteric-coated particles comprising a PPI such as Omeprazole is disclosed for example in U.S. Pat. Nos. 4,786,505 and 4,853,230.

The compositions of the present invention comprise a PPI in an effective amount to achieve a pharmacological effect or therapeutic improvement without undue adverse side effects. A therapeutic improvement includes but is not limited to: raising of gastric pH, reduced gastrointestinal bleeding, or improvement or elimination of symptoms. According to a preferred embodiment, the typical daily dose of the PPI varies and will depend on various factors such as the individual requirements of the patients and the disease to be treated. In general, the daily dose of PPI will be in the range of 1-400 mg. A preferred standard approximate amount of a PPI present in the composition is typically about 20-80 mg of omeprazole, about 30 mg lansoprazole, about 40 mg pantoprazole, about 20 mg rabeprazole, and the pharmacologically equivalent doses of the following PPIs: habeprazole, pariprazole, dontoprazole, ransoprazole, perprazole (s-omeprazole magnesium), tenatoprazole and leminoprazole.

The active ingredients of the present invention are preferably formulated in a single oral dosage form containing all active ingredients. The compositions of the present invention may be formulated in either solid or liquid form. It is noted that solid formulations are preferred in view of the improved stability of solid formulations as compared to liquid formulations and better patient compliance.

In one embodiment, the PPI particles and one or more aliphatic carboxylic acid derivatives are formulated in a single solid dosage form such as multi-layered tablets, suspension tablets, effervescent tablets, powder, pellets, granules or capsules comprising multiple beads as well as a capsule within a capsule or a double chambered capsule. In another embodiment, the active agents may be formulated in a single liquid dosage form such as suspension containing all active ingredients or dry suspension to be reconstituted prior to use.

The acid-labile PPI particles in the present composition are preferably formulated as enteric-coated delayed-release granules or as granules coated with non-enteric time-dependent release polymers in order to avoid contact with the gastric juice. Non-limiting examples of suitable pH-dependent enteric-coated polymers to be used in the present invention are: cellulose acetate phthalate, hydroxypropylmethylcellulose phthalate, polyvinylacetate phthalate, methacrylic acid copolymer, shellac, hydroxypropylmethylcellulose succinate, cellulose acetate trimellitate, and mixtures of any of the foregoing. A suitable commercially available enteric material, for example, is sold under the trademark Eudragit L 100-55. This coating can be spray coated onto the substrate.

Non-enteric-coated time-dependent release polymers include, for example, one or more polymers that swell in the stomach via the absorption of water from the gastric fluid, thereby increasing the size of the particles to create thick coating layer. The time-dependent release coating generally possesses erosion and/or diffusion properties that are independent of the pH of the external aqueous medium. Thus, the active ingredient is slowly released from the particles by diffusion or following slow erosion of the particles in the stomach.

Suitable non-enteric time-dependent release coatings are for example: film-forming compounds such as cellulosic derivatives, such as methylcellulose, hydroxypropyl methylcellulose (HPMC), hydroxyethylcellulose, and/or acrylic polymers including the non-enteric forms of the Eudragit brand polymers. Other film-forming materials may be used alone or in combination with each other or with the ones listed above. These other film forming materials generally include poly(vinylpyrrolidone), Zein, poly(ethylene glycol), poly(ethylene oxide), poly(vinyl alcohol), poly(vinyl acetate), and ethyl cellulose, as well as other pharmaceutically acceptable hydrophilic and hydrophobic film-forming materials. These film-forming materials may be applied to the substrate cores using water as the vehicle or, alternatively, a solvent system. Hydro-alcoholic systems may also be employed to serve as a vehicle for film formation.

Other materials which are suitable for making the time-dependent release coating of the invention include, by way of example and without limitation, water soluble polysaccharide gums such as carrageenan, fucoidan, gum ghatti, tragacanth, arabinogalactan, pectin, and xanthan; water-soluble salts of polysaccharide gums such as sodium alginate, sodium tragacanthin, and sodium gum ghattate; water-soluble hydroxyalkylcellulose wherein the alkyl member is straight or branched of 1 to 7 carbons such as hydroxymethylcellulose, hydroxyethylcellulose, and hydroxypropylcellulose; synthetic water-soluble cellulose-based lamina formers such as methyl cellulose and its hydroxyalkyl methylcellulose cellulose derivatives such as a member selected from the group consisting of hydroxyethyl methylcellulose, hydroxypropyl methylcellulose, and hydroxybutyl methylcellulose; other cellulose polymers such as sodium carboxymethylcellulose; and other materials known to those of ordinary skill in the art. Other lamina forming materials that can be used for this purpose include poly(vinylpyrrolidone), polyvinylalcohol, polyethylene oxide, a blend of gelatin and polyvinyl-pyrrolidone, gelatin, glucose, saccharides, povidone, copovidone, poly(vinylpyrrolidone)-poly(vinyl acetate) copolymer.

In one specific example, the composition of the present invention is formulated as a single dosage form comprising multiple beads contained in hard gelatin capsules. The capsules contain mixed population of beads selected from: beads comprising enteric-coated PPI or beads comprising PPI coated with time-dependent release polymer, and beads comprising one or more aliphatic carboxylic acid derivatives either non-coated or coated with hydroxypropyl methylcellulose or alginate. The different population of beads may each be contained in a different capsule while those capsules are contained within a single capsule.

In yet another example, the compositions of the present invention are formulated as press-coat or double-layered tablets comprising enteric-coated PPI in one layer and aliphatic carboxylic acid derivatives either non-coated or coated with hydroxypropyl methylcellulose in a second layer.

In a further example, the compositions of the present invention may be formulated as two layer non-aqueous semi-solid fill into hard gelatin capsules in which the PPI is solubilized in a lipid base (non-aqueous, quick release) which is liquid above room temperature but forms a semi-solid on cooling and can therefore be filled into hard gelatin capsules.

The active ingredients of the present invention may be formulated in a multiple oral dosage forms in which the aliphatic carboxylic acid derivative is administered in a separate dosage form but in conjugation with the PPI. For example, the aliphatic carboxylic acid derivative may be formulated in oral suspension or a solid dosage form such as capsules, tablets, suspension tablets, or effervescent tablets and the PPI may be formulated in a separate solid dosage form, preferably enteric-coated beads or time-dependent release beads contained in capsules or tablets.

When using multiple oral dosage forms, the aliphatic carboxylic acid derivative can be administered before, simultaneously with, or after the PPI. In sequential administration, there may be some substantial delay (e.g., minutes or even few hours) between the administration of the aliphatic carboxylic acid derivative and the PPI as long as the aliphatic carboxylic acid derivative has exerted some physiological effect when the PPI is administered or becomes active. In a preferred embodiment, the PPI administered is in the enteric-coated or the time-dependent release form. According to this embodiment, it is not necessary that the PPI administration precedes the aliphatic carboxylic acid derivative administration since the derivatives possess delayed and/or sustained enhancement effect on the PPI activity compared to the non-derivatized acid molecules.

It is also possible to add buffering agents to the formulation in order to facilitate the release of the PPI from the enteric-coated pellets, thereby enhancing the absorption of the PPI in blood. Specifically, a buffering agent such as for example sodium bicarbonate may be added in an amount sufficient to provide a pH above 5 in the stomach. For example, between 300 to 2,000 mg of sodium bicarbonate may be added to the formulation. If fast absorption of PPI in blood is required, it is possible to use non-enteric PPI pellets in the present formulations. In this case, the stability of the PPI in the stomach will be preserved due to the buffering agent that provides a pH above 5 in the stomach.

The active ingredients of the present invention may be incorporated within inert pharmaceutically acceptable beads. In this case, the drug(s) may be mixed with further ingredients prior to being coated onto the beads. Ingredients include, but are not limited to, binders, surfactants, fillers, disintegrating agents, alkaline additives or other pharmaceutically acceptable ingredients, alone or in mixtures. Binders include, for example, celluloses such as hydroxypropyl methylcellulose, hydroxypropyl cellulose and carboxymethyl-cellulose sodium, polyvinyl pyrrolidone, sugars, starches and other pharmaceutically acceptable substances with cohesive properties. Suitable surfactants include pharmaceutically acceptable non-ionic or ionic surfactants. An example of a suitable surfactant is sodium lauryl sulfate.

The particles may be formed into a packed mass for ingestion by conventional techniques. For instance, the particles may be encapsulated as a "hard-filled capsule" using known encapsulating procedures and materials. The encapsulating material should be highly soluble in gastric fluid so that the particles are rapidly dispersed in the stomach after the capsule is ingested.

In another embodiment, the active ingredients of the present invention are packaged in compressed tablets. The term "compressed tablet" generally refers to a plain, uncoated tablet for oral ingestion, prepared by a single compression or by pre-compaction tapping followed by a final compression. Such solid forms can be manufactured as is well known in the art. Tablet forms can include, for example, one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmaceutically compatible carriers. The manufacturing processes may employ one, or a combination of, four established methods: (1) dry mixing; (2) direct compression; (3) milling; and (4) non-aqueous granulation. Lachman et al., The Theory and Practice of Industrial Pharmacy (1986). Such tablets may also comprise film coatings, which preferably dissolve upon oral ingestion or upon contact with diluent.

In another alternative, the compositions of the present invention are formulated in compressed forms, such as suspension tablets and effervescent tablets, such that upon reaction with water or other diluents, the aqueous form of the composition is produced for oral administration. These forms are particularly useful for medicating children and the elderly and others in a way that is much more acceptable than swallowing or chewing a tablet. The present pharmaceutical tablets or other solid dosage forms disintegrate the alkaline agent with minimal shaking or agitation.

The term "suspension tablets" as used herein refers to compressed tablets which rapidly disintegrate after they are placed in water, and are readily dispersible to form a suspension containing a precise dosage of the PPI and the PPI enhancer. To achieve rapid disintegration of the tablet, a disintegrant such as croscarmellose sodium may be added to the formulation. The disintegrant may be blended in compressed tablet formulations either alone or in combination with microcrystalline cellulose, which is well known for its ability to improve compressibility of difficult to compress tablet materials. Microcrystalline cellulose, alone or co-processed with other ingredients, is also a common additive for compressed tablets and is well known for its ability to improve compressibility of difficult to compress tablet materials. It is commercially available under the Avicel trademark.

The suspension tablet composition may, in addition to the ingredients described above, contain other ingredients often used in pharmaceutical tablets, including flavoring agents, sweetening agents, flow aids, lubricants or other common tablet adjuvants, as will be apparent to those skilled in the art. Other disintegrants, such as crospividone and sodium starch glycolate may be employed, although croscarmellose sodium is preferred.

In addition to the above ingredients, the oral dosage forms described above may also contain suitable quantities of other materials, e.g. diluents, lubricants, binders, granulating aids, colorants, flavorants and glidants that are conventional in the pharmaceutical art. The quantities of these additional materials will be sufficient to provide the desired effect to the desired formulation. Specific examples of pharmaceutically acceptable carriers and excipients that may be used to formulate oral dosage forms are described in the Handbook of Pharmaceutical Excipients, American Pharmaceutical Association (1986), incorporated by reference herein.

For parenteral administration, the active ingredients are preferably administered by intravenous, subcutaneous, intramuscular injection or buccal (for example, sublingual) administration, in compositions with pharmaceutically acceptable vehicles or carriers. For administration by injection, it is preferred to use the active ingredients in solution in a sterile aqueous vehicle, which may also contain other solutes such as buffers or preservatives as well as sufficient quantities of pharmaceutically acceptable salts or of glucose to make the solution isotonic with respect to blood. In formulating the pharmaceutical composition into the form of a solution or suspension, all diluents customarily used in the art can be used. Examples of suitable diluents are water, ethyl alcohol, propylene glycol, ethoxylated isostearyl alcohol, polyoxyethylene sorbitol, and sorbitan esters. Sodium chloride, glucose or glycerol may be incorporated into a therapeutic agent in an amount sufficient to prepare an isotonic solution. The therapeutic agent may further contain ordinary dissolving aids, buffers, and preservatives, and optionally, coloring agents, fragrances, flavors, sweeteners, and other pharmacologically active agents which are known in the art.

For buccal delivery, either one of the active ingredients or both are formulated in a formulation designed to allow for delivery across the oral mucosa. Transmucosal delivery of PPI and/or aliphatic carboxylic acid molecules provides an alternative route of administration that rapidly increases plasma levels of the active ingredients. Transmucosal delivery systems are disclosed for example in U.S. Pat. Nos. 5,137,729, 6,159,498 and 5,800,832. It is preferable that the PPI is delivered via transmucosal delivery and the aliphatic carboxylic acid or derivative thereof such as succinic acid or the methyl ester derivative thereof are delivered via oral tablets or capsule. Thus, PPI may be formulated for transmucosal (buccal) delivery and the aliphatic carboxylic derivative molecules may be formulated for oral (tablets, capsule) delivery, in either separate or single-unit dosage form.

The dosage of the aliphatic carboxylic derivative molecules of the present invention may be in the range from about 1 to 100 mg/kg body weight, preferably from about 1 to 10 mg/kg body weight by parenteral administration per day in multiple dose, depending upon the type of disease, the severity of condition to be treated, and the like.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1

Figure 1:
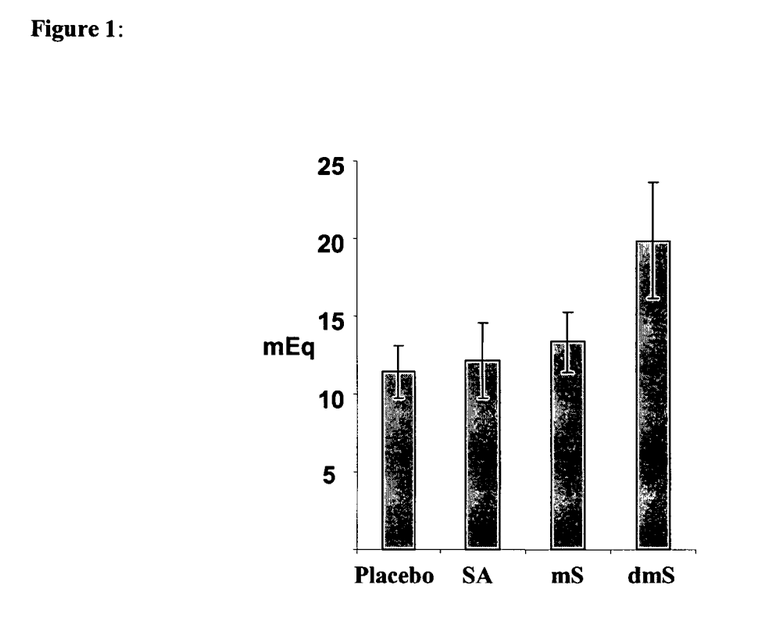
FIG. 1 demonstrates that succinic acid dimethyl ester is capable of enhancing gastric acid output even after 60 minutes from dosing.

Stimulation of Gastric Acid Secretion Following Oral Administration of Sodium Succinate, Monomethylester or Dimethyl Ester of Succinic Acid in Rats Rats were administered (per os) with succinic acid (SA, 14.88 mg/kg), monomethylester of succinic acid (mS, 16.65 mg/kg) or dimethyl ester of succinic acid (dmS, 17.65 mg/kg) using gavage. 60 minutes later the rats were anesthetized with ketamine/domitor and the pylorus was ligated. Following additional 30 min, gastric juice was collected from the gastric lumen. Acid output was determined by titration with NaOH. Total acid output expressed in mEq HCl was calculated by multiplying the sample volume by the acid concentration. Results are expressed as means±SEM of 8 animals from each experimental group. As demonstrated in FIG. 1, oral administration of dimethyl ester of succinic acid (dmS) as well as the monomethyl ester of succinic acid (mS) were effective in enhancing gastric output. SA did not show an effect when given 60 minutes prior to pylorus ligation. These results indicate that the dimethyl ester and momomethyl ester derivatives of succinic acid are capable in enhancing gastric acid output even after 60 minutes from dosing, suggesting delayed or sustained effect of the derivatives on gastric acid output compared to the non-derivatized succinic acid.

Example 2

Dimethyl Ester of Succinic Acid is Capable of Enhancing the Activity of Pantoprazole on Gastric Acid Secretion To further study the delayed or sustained enhancement effect of dimethyl ester of succinic acid on the activity of pantoprazole, an experimental model of conscious pylorus-ligated rats was used. This experimental model permits the analysis of the effect of drugs on gastric acid secretion in conscious animals and avoids the effect of anesthesia on gastric acid secretion. Pantoprazole alone (3 mg/ml) or in combination with succinic acid (SA, 14.88 mg/kg) or dimethyl ester of succinic acid (dmS, 17.65 mg/kg) were administered by oral gavage. The succinates were administered 30 min prior to the administration of pantoprazole in order to test the sustained or delayed effect of dimethyl ester of succinic acid compared to the non-derivatized succinic acid. 120 min post succinates administration, the animals were anesthetized using anesthetic gas machine for a short period (5 minutes) that is sufficient to perform the pylorus ligation procedure and to close the abdomen. The animals were then placed back into its cage for additional 110 min after which the animals were sacrificed. The ligature was placed around the esophagus, the stomach removed and gastric content was collected. Following centrifugation, the gastric output and the pH of the gastric juice samples was determined. Data is presented as mean±SEM of gastric output. The number of animals is 6-7 in each experimental group.

Figure 2:
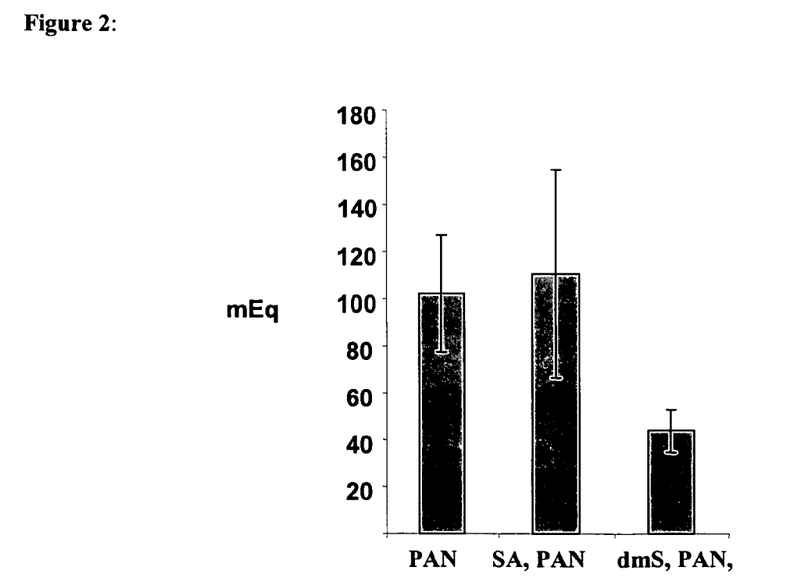
FIG. 2 demonstrates that dimethyl ester of succinic acid is capable of enhancing the activity of pantoprazole on gastric acid secretion when the dimethyl ester of succinic acid was administered 30 min prior to the administration of pantoprazole.

As can be seen in FIG. 2, when the succinates were administered 30 min prior to the administration of pantoprazole, only dimethyl ester of succinic acid was capable of enhancing the effect of PPI on gastric acid output. These results support a delayed or sustained enhancement effect of the dimethyl ester derivative on the PPI activity compared to the non-derivatized succinic acid.

Example 3

Oral Formulations Comprising a Proton Pump Inhibitor (PPI) and Dimethyl Ester of Succinic Acid Hard Gelatin Capsules Hard gelatin capsules may contain a mixed granules population of dimethyl ester of succinic acid (DMS) and PPI. DMS is in an immediate release formulation and PPI is formulated as enteric-coated granules or time-dependent release coating (delayed release). Granules may be packed into a hard gelatin capsule in an amount corresponding to 40 mg PPI and 600-700 mg DMS per capsule. Alternatively, each compound may be packed in an individual capsule while those capsules are packed together in a single capsule. Another possibility is that each compound may be separated using a double chambered capsule.

A) Immediate release DMS formulation:
40 mg enteric-coated (Eudragit) or time-dependent release coated (HPMC) PPI granules
600-700 mg DMS
diluent Tablets or Caplets The pharmaceutical composition may be in the form of tablet or more preferably caplet. The caplet contains a mixed of DMS (immediate release as mentioned above), enteric-coated or time-dependent release coated PPI (stable under compression pressure) and a wide variety of conventional tableting aid agents to be compressed into a caplet formulation.

Powder for Oral Suspension

Powder for oral suspension is comprised of DMS and enteric-coated or time-dependent release coated PPI granules. DMS is in immediate release formulation (as mentioned above). PPI are formulated as enteric-coated or time-dependent release coated granules (delayed release). The composition comes in individual packets to be constituted with water. When mixed with water, powder becomes a uniform liquid suspension.

Injectable Preparation

A PPI and DMS liquid solution is prepared by dissolving DMS and PPI in 0.9% sodium chloride solution. To prepare a physiological 0.9% sodium chloride solution for dissolution of PPI and DMS, a concentrated (10 times) solution of 9% sodium chloride solution is diluted to obtain a 1× solution. To prepare a dose form for intravenous administration, PPI and DMS are dissolved in 10 ml of 0.9% sodium chloride solution at concentrations of 4 mg/ml and 60 mg/ml, respectively, and the resulting solution may be used in intravenous administration of the compounds.

It will be appreciated by a person skilled in the art that the present invention is not limited by what has been particularly shown and described hereinabove. Rather, the scope of the invention is defined by the claims that follow.

The invention claimed is:

1. A pharmaceutical composition wherein the active ingredients consist of a pharmaceutically effective amount of:
   (i) a parietal cell activator comprising one or more aliphatic carboxylic acid derivatives, wherein the one or more derivatives of aliphatic carboxylic acid is monomethyl or dimethyl ester of succinic acid; and
   (ii) an irreversible gastric $H^+/K^+$-ATPase proton pump inhibitor (PPI), wherein the PPI particles are formulated as enteric-coated delayed release granules or as granules coated with non-enteric time-dependent release polymers, wherein the derivatives possess delayed, sustained, or both delayed and sustained parietal cell activation compared to non-derivatized acid molecules, wherein the one or more aliphatic carboxylic acid derivatives in conjunction with the PPI reduces gastric acid secretion in the stomach, wherein a ratio between the one or more derivatives of aliphatic carboxylic acid molecules and the PPI is about 20:1 to about 1:5, and wherein the active ingredients are formulated as:
   (a) press-coat or double-layered tablets comprising the enteric-coated PPI in one layer and the aliphatic carboxylic acid derivatives either non-coated or coated with hydroxypropyl methylcellulose in a second layer;
   (b) a single dosage form comprising hard gelatin capsules comprising a mixed population of beads selected from the PPI particles and beads comprising one or more of the aliphatic carboxylic acid derivatives either non-coated or coated with hydroxypropyl methylcellulose or alginate; or
   (c) a solid dosage form, wherein the solid dosage form is a capsule or a multi-layered tablet containing the PPI particles and particles of the aliphatic carboxylic acid derivative.

2. The composition of claim 1, in a form suitable for oral administration.

3. The composition of claim 2, wherein the one or more derivatives of aliphatic carboxylic acid molecule is monomethyl or dimethyl ester of succinic acid in an amount of between 50 and 1000 mg.

4. The composition of claim 1, wherein the PPI is granulated into beads and the one or more derivatives of aliphatic carboxylic acid molecules are formulated in immediate release formulation.

5. The composition of claim 1, wherein the PPI is selected from the group consisting of: rabeprazole, omeprazole, esomeprazole, lansoprazole, pantoprazole, leminoprazole, tenatoprazole, single enantiomers thereof, alkaline salts thereof and mixtures thereof.

6. A pharmaceutical kit wherein the active ingredients consist of a pharmaceutically effective amount of:
   (i) a parietal cell activator comprising one or more aliphatic carboxylic acid derivatives, wherein the one or more derivatives of aliphatic carboxylic acid is monomethyl or dimethyl ester of succinic acid; and
   (ii) an irreversible gastric $H^+/K^+$-ATPase proton pump inhibitor (PPI), wherein the PPI particles are formulated as enteric-coated delayed release granules or as granules coated with non-enteric time-dependent release polymers, wherein the derivatives possess delayed, sustained, or both delayed and sustained parietal cell activation compared to non-derivatized acid molecules, wherein the one or more aliphatic carboxylic acid derivatives in conjunction with the PPI reduces gastric acid secretion in the stomach, wherein a ratio between the one or more derivatives of aliphatic carboxylic acid molecules and the PPI is about 20:1 to about 1:5, and wherein the active ingredients are formulated as:
(a) press-coat or double-layered tablets comprising the enteric-coated PPI in one layer and the aliphatic carboxylic acid derivatives either non-coated or coated with hydroxypropyl methylcellulose in a second layer;
(b) a single dosage form comprising hard gelatin capsules comprising a mixed population of beads selected from the PPI particles and beads comprising one or more of the aliphatic carboxylic acid derivatives either non-coated or coated with hydroxypropyl methylcellulose or alginate; or
(c) a solid dosage form, wherein the solid dosage form is a capsule or a multi-layered tablet containing the PPI particles and particles of the aliphatic carboxylic acid derivative.

7. A method of reducing gastric acid secretion in a mammal, the method comprising administering to the mammal an effective amount of the composition of claim 1.

8. The method of claim 7, wherein the disorder is selected from the group consisting of: esophagitis, gastritis, duodenitis, peptic ulcer, duodenal ulcer, pathologies associated with nonsteroidal anti-inflammatory drugs (NSAID), non-ulcer (functional) Dyspepsia, gastroesophageal reflux disease, gastrinomas, acute upper gastrointestinal bleeding, stress ulceration, *Helicobacter pylori* infections, Zollinger-Ellison syndrome (ZES), Werner's syndrome, and systemic mastocytosis.

9. The method of claim 8, wherein the mammal is a human subject.

10. The method of claim 9, wherein the one or more derivatives of aliphatic carboxylic acid molecules are formulated in immediate release formulation and are administered simultaneously with administration of the PPI.

11. The method of claim 7, wherein the one or more derivatives of aliphatic carboxylic acid molecules in conjunction with an effective amount of the PPI are administered via oral route of administration.

12. A pharmaceutical composition wherein the active ingredients consist of a pharmaceutically effective amount of:
(i) a parietal cell activator comprising one or more aliphatic carboxylic acid derivatives, wherein the one or more derivatives of aliphatic carboxylic acid is monomethyl or dimethyl ester of succinic acid;
(ii) an irreversible gastric $H^+/K^+$-ATPase proton pump inhibitor (PPI), and
(iii) one or more non-derivatized aliphatic carboxylic acid molecules wherein the PPI particles are formulated as enteric-coated delayed release granules or as granules coated with non-enteric time-dependent release polymers, wherein the derivatives possess delayed, sustained, or both delayed and sustained parietal cell activation compared to non-derivatized acid molecules, wherein the one or more aliphatic carboxylic acid derivatives in conjunction with the PPI reduces gastric acid secretion in the stomach, wherein a ratio between the one or more derivatives of aliphatic carboxylic acid molecules and the PPI is about 20:1 to about 1:5, and wherein the active ingredients are formulated as:
(a) press-coat or double-layered tablets comprising the enteric-coated PPI in one layer and the aliphatic carboxylic acid derivatives either non-coated or coated with hydroxypropyl methylcellulose in a second layer;
(b) a single dosage form comprising hard gelatin capsules comprising a mixed population of beads selected from the PPI particles and beads comprising one or more of the aliphatic carboxylic acid derivatives either non-coated or coated with hydroxypropyl methylcellulose or alginate; or
(c) a solid dosage form, wherein the solid dosage form is a capsule or a multi-layered tablet containing the PPI particles and particles of the aliphatic carboxylic acid derivative.

13. The pharmaceutical composition of claim 12, wherein the non-derivatized aliphatic carboxylic acid molecule is succinic acid and the aliphatic carboxylic acid derivative is dimethyl ester of succinic acid.

14. A pharmaceutical composition wherein the active ingredients consist of a pharmaceutically effective amount of:
(i) a parietal cell activator comprising one or more aliphatic carboxylic acid derivatives, wherein the one or more derivatives of aliphatic carboxylic acid is monomethyl or dimethyl ester of succinic acid;
(ii) an irreversible gastric $H^+/K^+$-ATPase proton pump inhibitor (PPI), and
(iii) an antibiotic agent effective against bacteria residing in the stomach or an additional parietal cell activator selected from the group consisting of: chocolate, caffeine, buffering agents, peppermint oil, spearmint oil, theophylline, theobromine, and aromatic amino acids;

wherein the PPI particles are formulated as enteric-coated delayed release granules or as granules coated with non-enteric time-dependent release polymers, wherein the derivatives possess delayed, sustained, or both delayed and sustained parietal cell activation compared to non-derivatized acid molecules, wherein the one or more aliphatic carboxylic acid derivatives in conjunction with the PPI reduces gastric acid secretion in the stomach, wherein a ratio between the one or more derivatives of aliphatic carboxylic acid molecules and the PPI is about 20:1 to about 1:5, and wherein the active ingredients are formulated as:
(a) press-coat or double-layered tablets comprising the enteric-coated PPI in one layer and the aliphatic carboxylic acid derivatives either non-coated or coated with hydroxypropyl methylcellulose in a second layer;
(b) a single dosage form comprising hard gelatin capsules comprising a mixed population of beads selected from the PPI particles and beads comprising one or more of the aliphatic carboxylic acid derivatives either non-coated or coated with hydroxypropyl methylcellulose or alginate; or
(c) a solid dosage form, wherein the solid dosage form is a capsule or a multi-layered tablet containing the PPI particles and particles of the aliphatic carboxylic acid derivative.

* * * * *